(12) United States Patent
Khan et al.

(10) Patent No.: US 10,568,522 B2
(45) Date of Patent: Feb. 25, 2020

(54) SURGICAL VISION AUGMENTATION SYSTEM

(71) Applicant: The Trustees of Dartmouth College, Hanover, NH (US)

(72) Inventors: Shadab Khan, Lebanon, NH (US); Ryan Halter, Orford, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 252 days.

(21) Appl. No.: 15/031,826

(22) PCT Filed: Oct. 23, 2014

(86) PCT No.: PCT/US2014/062002
§ 371 (c)(1),
(2) Date: Apr. 25, 2016

(87) PCT Pub. No.: WO2015/061588
PCT Pub. Date: Apr. 30, 2015

(65) Prior Publication Data
US 2016/0249811 A1    Sep. 1, 2016

Related U.S. Application Data

(60) Provisional application No. 61/894,704, filed on Oct. 23, 2013.

(51) Int. Cl.
*A61B 5/00* (2006.01)
*A61B 5/01* (2006.01)
(Continued)

(52) U.S. Cl.
CPC .......... *A61B 5/0086* (2013.01); *A61B 1/0005* (2013.01); *A61B 1/00009* (2013.01);
(Continued)

(58) Field of Classification Search
CPC . A61B 5/0086; A61B 1/00009; A61B 1/0638; A61B 1/0005; A61B 1/128;
(Continued)

(56) References Cited

U.S. PATENT DOCUMENTS 6,009,340 A * 12/1999 Hsia ................. A61B 5/00
348/164
6,023,637 A * 2/2000 Liu ................. A61B 5/015
128/922

(Continued)

OTHER PUBLICATIONS

PCT/US2014/062002 International Search Report & Written Opinion dated Mar. 25, 2015, 10 pages.

*Primary Examiner* — Sanjay Cattungal
(74) *Attorney, Agent, or Firm* — Lathrop GPM LLP

(57) ABSTRACT

A surgical vision system for imaging heat capacity and cooling rate of tissue has an infrared source configured to provide infrared light to tissue, the infrared light sufficient to heat tissue, and an infrared camera configured to provide images of tissue at infrared wavelengths. The system also has an image processing system configured to determine, from the infrared images of tissue, a cooling or heating rate
(Continued)

at pixels of the images of tissue at infrared wavelengths and to display images derived from the cooling rate at the pixels.

17 Claims, 3 Drawing Sheets

(51) Int. Cl.
*A61B 1/12* (2006.01)
*A61B 1/00* (2006.01)
*A61B 1/06* (2006.01)
*A61B 1/04* (2006.01)
*A61B 1/313* (2006.01)

(52) U.S. Cl.
CPC ............... *A61B 1/04* (2013.01); *A61B 1/063* (2013.01); *A61B 1/0638* (2013.01); *A61B 1/128* (2013.01); *A61B 1/3132* (2013.01); *A61B 5/0035* (2013.01); *A61B 5/0075* (2013.01); *A61B 5/015* (2013.01); *A61B 5/6847* (2013.01); *A61B 2576/00* (2013.01)

(58) Field of Classification Search
CPC ... A61B 5/6847; A61B 5/0075; A61B 5/0035; A61B 1/3132; A61B 1/063; A61B 1/04; A61B 5/015; A61B 2576/00
USPC .................................................. 600/473–480
See application file for complete search history.

(56) References Cited

U.S. PATENT DOCUMENTS

| | | | |
|---|---|---|---|
| 6,652,452 | B1 | 11/2003 | Seifert et al. |
| 9,622,662 | B2 * | 4/2017 | Zuzak .................. A61B 5/0071 |
| 9,872,613 | B2 * | 1/2018 | Seibel .................. A61B 1/0008 |
| 2001/0055462 | A1 * | 12/2001 | Seibel ................ A61B 1/00048 385/147 |
| 2003/0044353 | A1 * | 3/2003 | Weissleder ........... C12Q 1/6816 424/9.6 |
| 2004/0019269 | A1 * | 1/2004 | Schaefer ............... A01J 5/0138 600/407 |
| 2004/0236225 | A1 * | 11/2004 | Murphy .................. A61B 5/015 600/473 |
| 2006/0195014 | A1 * | 8/2006 | Seibel .................. A61B 1/0008 600/102 |
| 2007/0173727 | A1 * | 7/2007 | Naghavi .................. A61B 5/01 600/483 |
| 2007/0213617 | A1 * | 9/2007 | Berman ............... A61B 5/0091 600/473 |
| 2010/0056928 | A1 * | 3/2010 | Zuzak .................. A61B 5/0071 600/476 |
| 2012/0190979 | A1 * | 7/2012 | McKenna ................ A61B 5/05 600/431 |

* cited by examiner

SURGICAL VISION AUGMENTATION SYSTEM

RELATED APPLICATIONS

This application is a 35 U.S.C. § 371 filing of International Application No. PCT/US2014/062002 filed Oct. 23, 2014, which claims priority to U.S. Provisional Patent Application 61/894,704 filed 23 Oct. 2013, the disclosure of which is incorporated by reference herein in its entirety.

FEDERAL FUNDING CLAUSE

This invention was supported by the National Institutes of Health grant number 1R01-CA143020-01A1. The Government has certain rights in the invention.

FIELD

The present document relates to the field of medical imaging devices for use during surgery.

BACKGROUND

Laparoscopic surgery has become common for minimally-invasive procedures. Laparoscopic surgery involves making a small number of small incisions, inserting surgical tools and a laparoscopic vision device having a light source and imaging apparatus through these openings to a surgical site, and then performing surgery within a body cavity. The body cavity is often enlarged by administering gas, such as carbon dioxide, to give the surgeon a larger, more exposed field of view. The surgical tools are typically manipulated directly by the surgeon or indirectly through a robotic-coupled apparatus that articulates based on how a surgeon manipulates a set of "joysticks". Laparoscopic surgery (both manual and robot-assisted) is particularly common for abdominal and pelvic procedures, including cholecystectomy and radical prostatectomy.

Similarly, endoscopic surgery has also become common for minimally-invasive surgical procedures in body cavities that communicate outside the body through a body opening. Endoscopic surgery involves threading an endoscope through the opening to a surgical site. The endoscope is a flexible device equipped with a light source and imaging apparatus, and typically having a lumen through which a gas, such as carbon dioxide, can be admitted to inflate the cavity to enable improved vision and through which a surgical tool may be threaded. Typically, an endoscope has manipulation or steering wires running from its head to a handle attached to its base so that the endoscope tip may be twisted or straightened by moving knobs on the handle. This allows threading of the endoscope through the body opening to the surgical site. Once the endoscope is threaded to the surgical site, surgical tools are threaded through the lumen of the endoscope and manipulated to perform the desired surgical procedure. The surgeon uses images obtained by the imaging apparatus of the endoscope to verify correct placement of the surgical tools, and to guide the surgery. Endoscopic surgery is often used for polypectomy in the colon, as well as transurethral prostatectomy and transurethral removal of bladder tumors (TURBT). Endoscopes are also often used for biopsies, including biopsies of the lung, colon, esophagus, and stomach. Endoscopes may be used for many other procedures than those listed here.

In typical laparoscopic and endoscopic procedures, a surgeon views the surgical site using the light source and optical imaging apparatus, and performs surgery under direction of images acquired by the imaging apparatus. The imaging apparatus used for the majority of endoscopic and laparoscopic procedures provides the surgeon with two-dimensional images of the surgical site. Recent robot-assisted systems have provided surgeon with a three-dimensional view of the surgical site through stereovision imaging devices. Since surgery is typically directed in accordance with optical images, it is desirable to have good contrast in the images between lesions or tissue needing removal and normal tissue of the subject that the surgeon intends to leave intact. While some tissues, like the gall bladder, have sharp color contrast relative to other nearby tissues, such as normal liver tissue, many other lesions and tumors have little color contrast relative to nearby tissues. Additionally, tissue surfaces are often difficult to visualize in images due to blood and other substances coating the surface.

In addition to contrast between normal and lesion tissue, it can be desirable to resolve differing types of normal tissues so that anatomy can be confirmed, or critical structures, such as nerves and blood vessels, can be left undamaged during the procedure.

SUMMARY

In an embodiment, a surgical vision system for imaging cooling rate of tissue has an infrared source configured to provide infrared light to tissue, the infrared light sufficient to heat tissue, and an infrared camera configured to provide images of tissue at infrared wavelengths. The system also has an image processing system configured to determine, from the infrared images of tissue, a cooling or heating rate at pixels of the images of tissue at infrared wavelengths and to display images derived from the cooling rate at the pixels.

In another embodiment, a surgical vision system for imaging the thermal energy of a tissue includes an infrared camera configured to provide images of tissue at infrared wavelengths and located in known orientation with respect to a camera operating in the visible spectrum; an infrared source, located on a secondary instrument, configured to provide infrared light to tissue; and an image processing system configured to determine the location and orientation of the secondary instrument by identifying where the infrared energy was deposited, and to display images derived from the images of tissue at infrared wavelengths. In yet another embodiment, a method of imaging tissue includes positioning an instrument selected from the group consisting of a laparoscope and an endoscope near the tissue, the instrument comprising a short-wavelength, or mid-wavelength infrared source and a corresponding infrared imager; using the infrared source to apply high-power infrared light to the tissue, and thereby heating the tissue; disabling the infrared source; acquiring a sequence of infrared images of the tissue while allowing heated tissue to cool; and processing the sequence of infrared images to produce an image depicting tissue cooling rate.

In yet another embodiment, a method of imaging tissue includes positioning an instrument selected from the group consisting of a laparoscope and an endoscope near the tissue, the instrument comprising a short-wavelength, or mid-wavelength infrared imager; positioning a second instrument near the tissue, the second instrument having a high-power infrared source; using the infrared source to apply high-power infrared light to the tissue, and thereby heating the tissue; disabling the infrared source; acquiring at least one infrared image of the tissue; and processing the infrared images to produce an image depicting a heated area of the tissue.

DETAILED DESCRIPTION OF THE EMBODIMENTS

Figure 1:
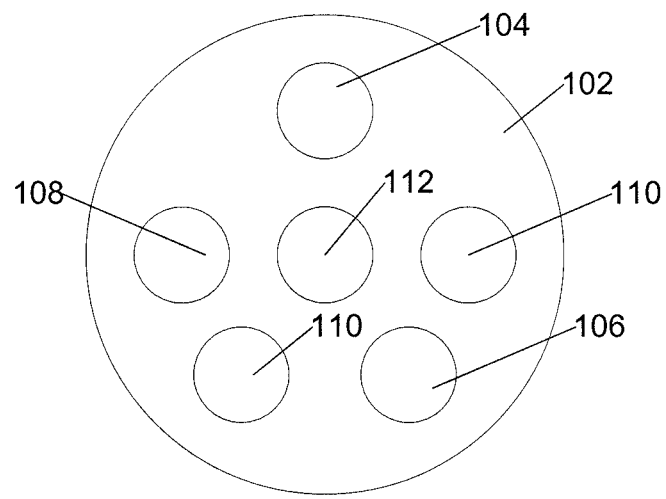
FIG. 1 is a schematic illustration of a head of an endoscope or laparoscope embodying the present device.
Figure 2:
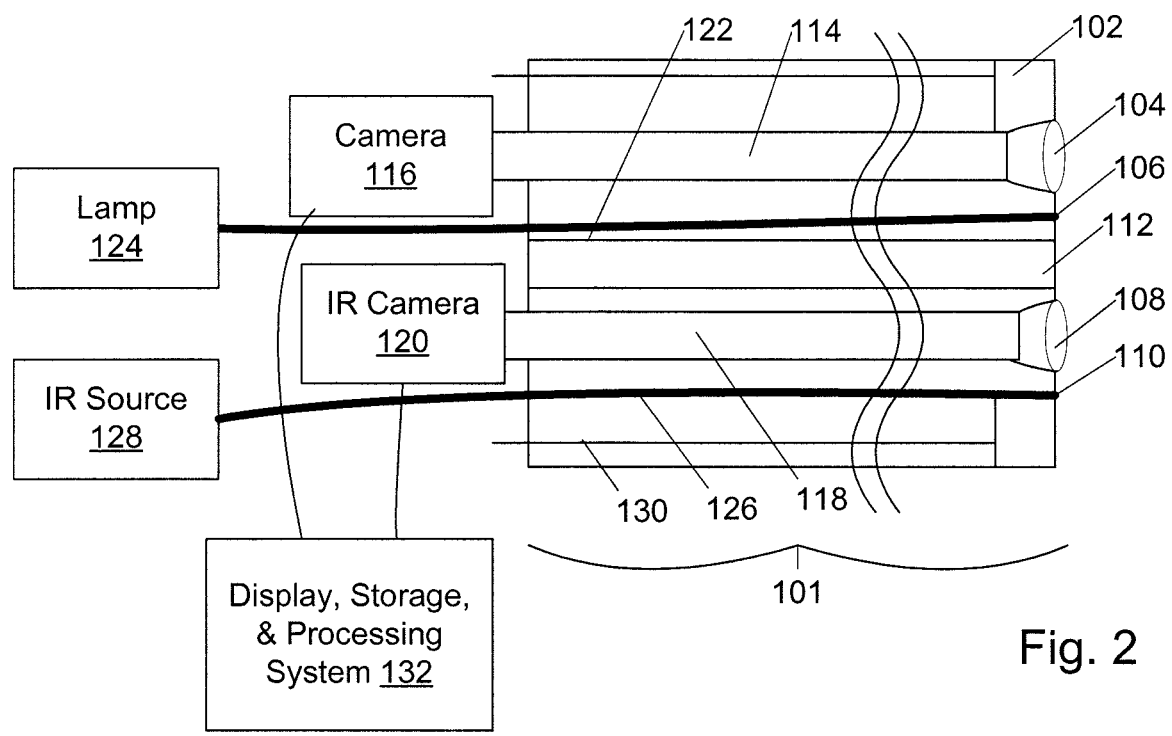
FIG. 2 is a schematic illustration of a cross section of an embodiment of an endoscope of FIG. 1.

An endoscope 101 has a head 102 (FIGS. 1 and 2) for insertion into a body cavity. The head has a viewport with an optical lens 104 configured to receive visible wavelength light, at least one visible-light illumination port 106, an infrared lens 108 configured to receive short-wavelength (0.8 micron to 1.8 micron), or middle-wavelength (1.8 micron to 4.5 micron) infrared light ranging between 0.8 and 4.5 micrometer wavelengths, and at least one infrared illumination port 110, with the lenses 104, 108 and illumination ports 106, 110 distributed around a lumen 112. The optical lens 104 is arranged to focus light onto a coherent fiber-optic bundle 114 capable of guiding visible-wavelength light into a camera 116, and the infrared lens 108 is arranged to focus light onto a coherent fiber-optic bundle 118 arranged to guide infrared-wavelength light into a mid-wavelength infrared camera 120. The visible-light illumination port 106 is coupled through an optical fiber or fiber bundle 122 to a visible-light illuminator 124, and the infrared illumination ports 110 through an infrared optical fiber or fiber bundle 126 to an infrared light source 128. The endoscope also has manipulation wires 130 arranged to deflect head 102 and controlled by knobs in a handle (not shown), as known in the art of endoscopy. Electronic optical camera 116 and infrared camera 120 are coupled to provide images to an image display, storage, and processing system 132. The endoscope is typically many times longer than its diameter; a scope may be less than one centimeter in diameter and two meters long between head and handle.

Figure 3:
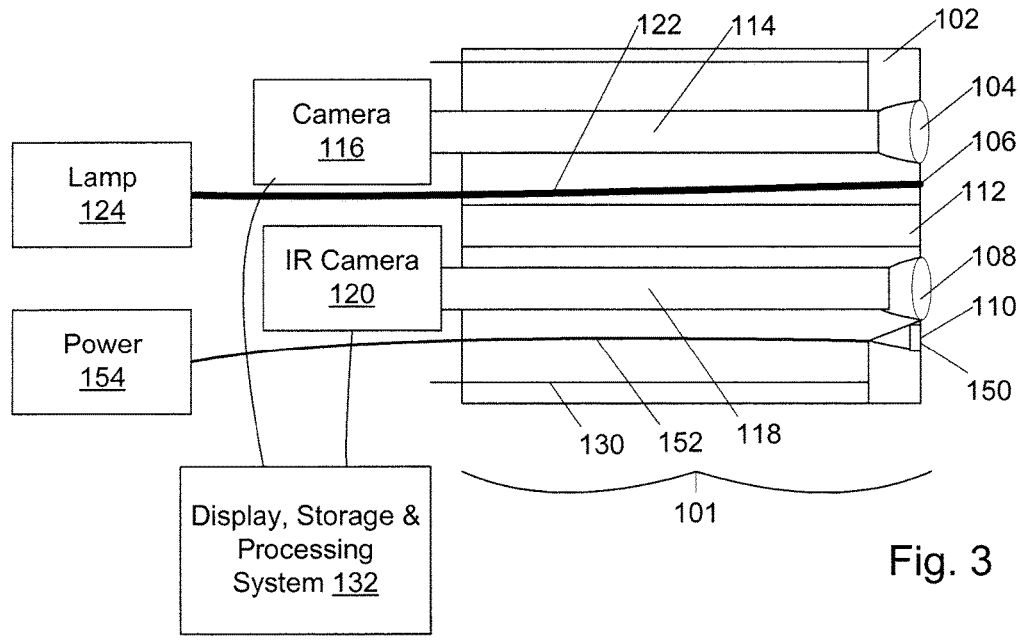
FIG. 3 is a schematic illustration of a cross section of an alternative embodiment of an endoscope.

In an alternative embodiment (FIG. 3), infrared optical fiber or fiber bundle 126 is replaced with an infrared light-emitting diode 150 driven through wires 152 in the endoscope by a controllable power supply 154.

In an alternative embodiment, a laparoscope is provided having features described above of endoscope 101, except that, since laparoscopes are typically rigid, there need be no manipulation wires 130 in a typical laparoscopic embodiment.

In an alternative embodiment, visible-light coherent fiber bundle 114 is deleted and camera 116 is located in endoscope tip 102 to provide image sensing. In an alternative embodiment, two optical lenses 104, two fiber bundles 114, and two cameras 116 are provided to enable stereo optical imaging, and provide three dimensional imaging of tissue or other objects that may be near endoscope head 102.

In an alternative embodiment, two optical lenses 104, two fiber bundles 114, and two cameras 116 are provided to enable stereo optical imaging, and one infrared illumination port 110, one infrared lens 198, and one infrared camera 120 is provided. The two cameras 116 are used to provide three dimensional imaging of tissue or other objects that may be near to the endoscopic head 102. The infrared camera is used to visualize the sub-surface morphology, and the information obtained from the infrared and visible range cameras together are used to augment the surgeon's vision of the surgical site.

In an embodiment, the infrared light emitting diode 150, or infrared source 128, uses an infrared light-emitting diode from ISBG, 26, Polytekhnicheskaya, 194021, St. Petersburg, Russia, and in an embodiment the light emitting diode is formed of InAsSb/InAsSbP semiconductors grown on InAs substrates to provide infrared of between 1.8 and 4.5 microns wavelength. In a particular embodiment, the midwavelength infrared light-emitting diode emits infrared energy with wavelengths between 2.5 and 3 microns. In another embodiment, the short-wavelength infrared light-emitting diodes with a wavelength of between 0.8 and 2.5 microns are used.

It is expected that infrared light in the infrared band of 0.8 to 4.5 microns wavelength will provide better heating, and better imaging of tissue temperature and tissue cooling, than practical with infrared light in the visible or near-infrared band having wavelengths less than 0.8 microns.

In an alternative embodiment, infrared source 128 has multiple infrared light-emitting diodes, each of which is capable of emitting infrared light at a separate wavelength in the 0.8 to 4.5 microns wavelength band; in a particular embodiment source 128 has at least one each of four or more medium-wavelength infrared (MWIR) LED types selected from the group of ISBG LEDs LED18, LED19, LED20, LED21, LED22, LED23, LED29, LED34, LED35, LED36, LED38, LED39, LED41, LED43, and LED46, so that it can provide light at fifteen particular separate wavelengths in the 1.8 to 4.5 micron band.

In an alternative embodiment, controllable infrared source 128 has one or more infrared lasers coupled to provide infrared light into fiber 126.

In an alternative embodiment, the endoscope/laparoscope does not have the infrared light source; instead a second instrument, not necessarily connected to the endoscope/laparoscope, is fitted with the infrared source or sources and used to heat the tissue. The endoscope/laparoscope is used to image the heating imposed by the secondary instrument fitted with the infrared source(s).

Figure 4:
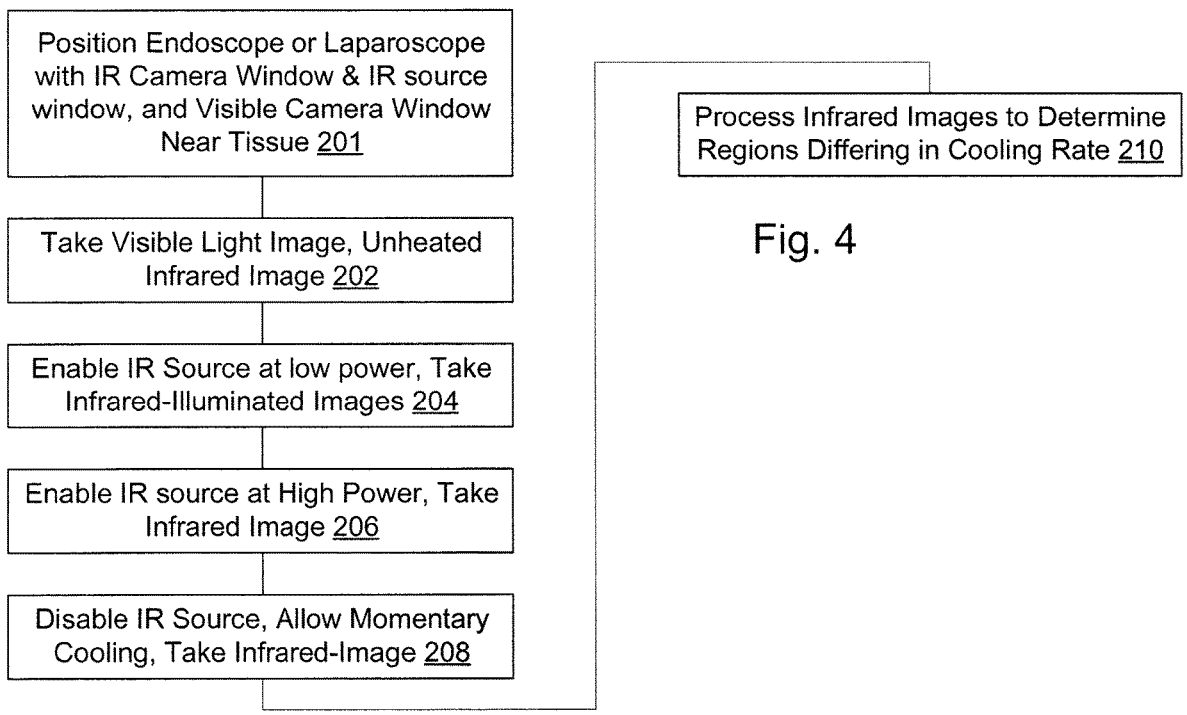
FIG. 4 is a flowchart of a method of imaging using the devices of FIG. 1 through FIG. 3.

In operation, the endoscope or laparoscope with IR camera window & IR source window, and visible camera window is positioned 201 (FIG. 4) near tissue of interest, typically under visual observation using white visible light from lamp 124 as imaged through optical lens 104, coherent bundle 114, and camera 116. Visual light images, and in some instances unheated, unlit infrared images of tissue, may then be captured 202. The infrared source 128, 150, is then enabled at low power and infrared images captured 204 under infrared lighting. In embodiments having multiple LED types in infrared source 128, an unheated, illuminated, infrared image is captured under low power light from each LED type present in the source. Images captured under each wavelength are compared by image display, storage, and processing system 132 to provide information about the tissue, including presence, absence, and location of vessels or tumors.

The infrared source 128 is then enabled at high power 206 to provide sufficient infrared energy that tissue near infrared source window 110 is heated by a temperature rise sufficient to be visible in the mid-wavelength infrared while not heating to the point where significant tissue damage occurs due to the short-term heating, such as to a temperature between 3-10 degrees Celsius above a body temperature of surrounding tissue, and in an embodiment to a temperature between 3 and 5 degrees Celsius above the body temperature, a temperature rise tolerated by most tissue types, and after or as tissue is heated an additional infrared image may be captured and processed by image processing system 132 to indicate a rate of heating of tissue.

In an embodiment, the high-power infrared light is enabled for a brief pulse of between 500 msec and 5 seconds, where the duration of the pulse is dependent on the location of the probe with respect to the tissue, available infrared source power, and the desired temperature rise.

After a brief pulse of high-power infrared light, the infrared source is then disabled, or in a variation reduced to low intensity below that intensity required for significant tissue heating, and an additional one or more images captured 208. These images are then processed 210 to provide images indicative of heating and cooling rate of the tissue. Tissue differs in cooling rate, for example tissue lying over large-bore blood vessels having rapid blood flow will cool more quickly than tissue distant from such large blood vessels. Similarly, different tissue types have different thermal properties; the heat capacity of different tissues types, such as benign and malignant tissues types, differs, and this difference provides a signature for discriminating tissue types. We model the temperature of a physical location in the IR image, using the corresponding infrared pixel intensity. By tracking the increase (in the case of heating) and/or decay (in the case of cooling) of pixel intensity over time, we fit a first- or second-order exponential decaying (cooling) or increasing (heating) function or other higher-order model to the data and create an image which shows the rate of decay or elevation of temperature associated with each pixel in the acquired IR image. This creates images representative of "Thermal Capacitance" or the rate at which tissues lose or gain temperature when thermal energy is applied. Such images are then enhanced using spatial or frequency-domain image processing code in image processing system 132 using methods including one or more of image denoising, image averaging, FFT-based filtering, and edge detection using a suitable method such as Prewitt, Canny, Sobel, Laplacian and other edge detection, as well as morphological operations and image segmentation to separate the region-of-interest from the background. Processed images are displayed to a surgeon for use in determining where and how deep to "cut," and what tissue or tissues to remove, while performing surgery. In embodiments, these images derived from heating and/or cooling rate at pixels are superimposed on, or alternated with, visible-light images to inform a surgeon of structures that are on, or lie below, the tissue surface and are not visible in visible-light images. The surgeon may then use this information in determining where and how deep to "cut" while performing surgery. This will be especially useful for identifying neurovascular structures, vascular structures, and evaluating surgical margins during tumor resection.

Figure 5:
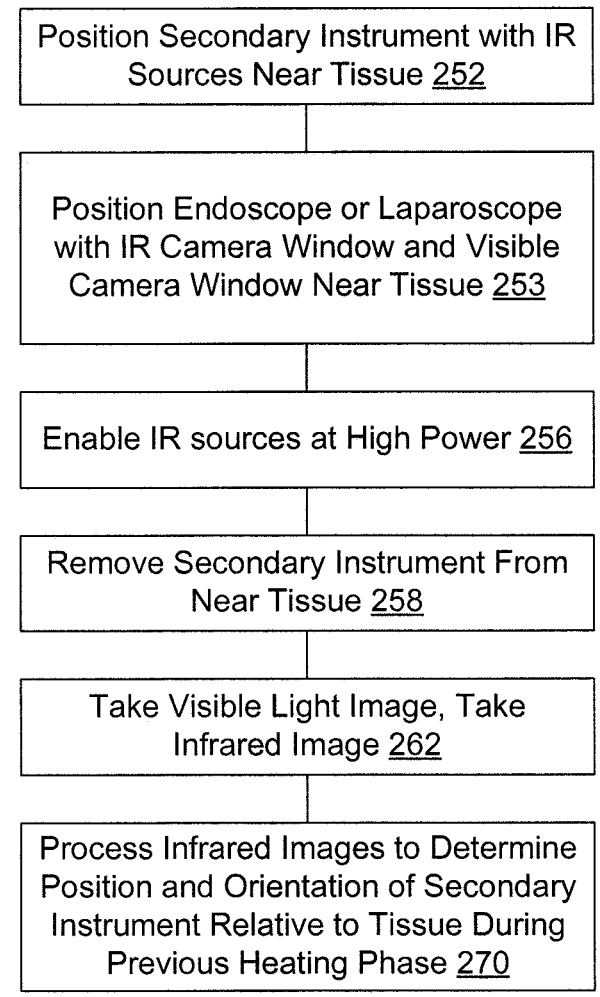
FIG. 5 is a flowchart of a method of using infrared imaging by a first instrument of heating of tissue produced by a second instrument to determine a position and orientation of the second instrument relative to tissue after removal of the second instrument.

In an embodiment in which the infrared source is located on a secondary instrument within the surgical space, the infrared camera system is used to identify the location, as illustrated in FIG. 5, in which the secondary instrument heated the tissue. In this embodiment, the infrared source or sources on the secondary instrument are energized while the instrument is positioned 252 near or in contact with the tissue; these sources deposit thermal energy into the tissue. The infrared camera system embodied in the laparoscope or endoscope is also positioned 253 near the tissue. When the secondary instrument is removed, the thermal energy deposited by the infrared sources is emitted from the tissue for some period of time as it cools. Images are acquired 262 in both visible and infrared light using the visible light and infrared cameras of the laparoscope or endoscope. The image processing system then processes 270 the images from the infrared camera on the endoscope or laparoscope to identify where this thermal energy is located on the tissue and, through computation, is able to specify precisely where on the tissue the secondary instrument was in contact. This method is useful during surgical procedures when the tissue region deforms during the contact with the secondary instrument; it can be challenging to identify where the secondary instrument was in contact with tissue after the instrument is removed from contact due to the tissue deforming back to it's unloaded state. This approach enables a surgeon to identify where the secondary instrument had been located even after the tissue deforms back to its unstressed state.

In a similar embodiment, the secondary instrument is equipped with additional tissue property sensors or imaging capabilities. It is important to identify these tissue properties to the surgeon by overlaying the sensed or imaged properties onto the visual feedback screen the surgeon has. The thermal imaging system is then used to identify where the probe was located so that these additional properties sensed can be registered to the correct location within visible spectrum images recorded with optical cameras, and composite images displayed for surgical guidance.

In a similar embodiment, the additional tissue properties sensed may be dependent on tissue temperature. By varying the temperature of the tissue using infrared heating, these additional tissue properties that are being sensed, will vary. This variation can be used in increase contrast between different tissue types. For example, the electrical bioimpedance of tissue is dependent on tissue temperature, and the change in bioimpedance with respect to change in temperature is not the same for all tissue types. If cancerous tissue and benign tissues have different temperature dependence, then increasing the temperature gives a wider contrast between malignant and benign bioimpedance parameters. Additional tissue properties including optical scatter and absorption at multiple frequencies, tissue density, acoustic impedance, and other may also be sensed as part of the secondary instrument.

Embodiments that observe a cooling rate at pixels of the infrared image are operable with an infrared imager sensitive to the same or similar wavelengths as the infrared source used for heating tissue, as well as at other wavelengths. Embodiments that observe a heating rate at pixels of the infrared image could, however, suffer undue interference if the infrared source used for heating tissue is at the same wavelength as the imager observing temperature; such embodiments may use an infrared source for heating at a different wavelength than imaging, and may equip the IR camera 120 with a blocking filter at the wavelength used for heating. Embodiments that use different wavelengths for heating and for imaging may have a low power illumination LED or other light source operable at the same wavelength used for imaging added to the infrared light source to provide illumination for unheated infrared imaging of the tissue.

Combinations

It is anticipated that the various features herein described may be combined in various ways, only some of which are listed here.

In a surgical vision system designated A for imaging a heating or cooling rate of tissue, the system has an infrared source configured to provide infrared light to tissue, the infrared light sufficient to heat a tissue surface to a temperature between 3 and 10 C above that of surrounding tissue, and an infrared camera configured to provide images of tissue at infrared wavelengths. The system also has an image processing system configured to determine, from the infrared images of tissue, the cooling or heating rate at pixels of the images of tissue at infrared wavelengths and to display images derived from the cooling or heating rate at the pixels.

A surgical vision system designated A1 including the vision system designated A wherein the infrared light is sufficient to heat a tissue surface to a temperature between 3 and 5 C above that of surrounding tissue.

A surgical vision system designated AA or A1 including the vision system designated A has the infrared source configured to provide infrared light to tissue through an end of an endoscope, and the infrared camera is configured to receive infrared light from tissue through the end of the endoscope.

A surgical vision system designated AB including the vision system designated A has the infrared source configured to provide infrared light to tissue through an end of a laparoscope, and the infrared camera is configured to receive infrared light from tissue through the end of the laparoscope.

A surgical vision system designated AC including the vision system designated A, A1, AA, or AB has the infrared camera operable at least at a first wavelength in the short-wavelength, or medium-wavelength infrared band of 0.8 to 4.6 microns.

A surgical vision system designated ACA including the vision system designated AC has the first wavelength in the medium-wavelength infrared band of 1.8 to 4.6 microns A surgical vision system designated AD including the vision system designated A, AA, AB, or AC has the infrared source is operable at least at a second wavelength in the short-wavelength, or medium-wavelength infrared band of 0.8 to 4.6 microns.

A surgical vision system designated ADA including the vision system designated AD wherein the second wavelength is in the medium-wavelength band of 1.8 to 4.6 microns.

A surgical vision system designated AE including the vision system designated AD wherein the second wavelength differs from the first wavelength.

A surgical vision system designated AF including the vision system designated AC, AD, or AE wherein the first wavelength lies between 2.5 and 3 microns.

A surgical vision system designated AG including the vision system designated A, AA, AB, AC, AD, AE, or AF wherein the images derived from the cooling or heating rate at the pixels are derived from the cooling rate.

A surgical vision system designated AH including the vision system designated A, AA, AB, AC, AD, AE, or AF wherein the rate of change of temperature at pixels of the images of tissue is the heating rate.

A surgical vision system designated B for imaging the thermal energy of tissue includes an infrared camera configured to provide images of tissue at infrared wavelengths and located in known orientation with respect to a camera operating in the visible spectrum; an infrared source, located on a secondary instrument, configured to provide infrared light to tissue; and an image processing system configured to determine the location and orientation of the secondary instrument by identifying where the infrared energy was deposited, and to display images derived from the images of tissue at infrared wavelengths.

A surgical vision system designated BA including the system designated B wherein the secondary instrument with the infrared source is fitted with multiple sources positioned in a specific pattern so that the image processing system can identify an orientation of the secondary instrument from the deposited infrared energy.

A surgical vision system designated BB including the system designated B or BA wherein the secondary instrument is configured to sense at least one additional tissue property including at least one of electrical bioimpedance, optical scattering, optical absorption, and tissue density.

A surgical vision system designated BC including the system designated BB wherein the at least one additional tissue property sensed is a property known to be a function of tissue temperature for at least one tissue type such that heating the tissue with the infrared source causes the additional tissue property to change.

A method of imaging tissue designated C includes positioning an instrument selected from the group consisting of a laparoscope and an endoscope near the tissue, the instrument including a mid-wavelength infrared source and a mid-wavelength infrared imager; using the infrared source to apply high-power infrared light to the tissue, and thereby heating the tissue; disabling the infrared source; acquiring a sequence of infrared images of the tissue while allowing heated tissue to cool; and processing the sequence of infrared images to produce an image depicting tissue cooling rate.

A method of imaging tissue designated CA including the method designated C and further including obtaining an optical image of the tissue with an optical imaging device of the instrument, and preparing a composite image derived from both the optical image and the image depicting tissue cooling rate.

A method of imaging tissue designated D includes positioning an instrument selected from the group consisting of a laparoscope and an endoscope near the tissue, the instrument including a mid-wavelength infrared imager; positioning a second instrument near the tissue, the second instrument having a high-power infrared source; using the infrared source to apply high-power infrared light to the tissue, and thereby heating the tissue; disabling the infrared source; acquiring at least one infrared image of the tissue; and processing the infrared images to produce an image depicting a heated area of the tissue.

It should be noted that the matter contained in the above description or shown in the accompanying drawings should be interpreted as illustrative and not in a limiting sense. The following claims are intended to cover generic and specific features described herein, as well as all statements of the scope of the present method and system.

What is claimed is:

1. A surgical vision system for imaging temperature changes of tissue, comprising:
   an infrared source configured to provide infrared light to tissue, the infrared light sufficient to heat a surface of the tissue to a temperature between 3 and 10 degrees Celsius above a temperature of surrounding tissue;
   an infrared camera configured to provide a sequence of infrared images of the tissue;

a camera adapted to obtain an optical image of the tissue; and an image processing system configured to determine an image of rate of elevation or decay of temperature of the tissue from the sequence of infrared images of the tissue by fitting a decay function to pixels of the sequence of infrared images of the tissue, the decay function being a first or second order exponential decay function.

2. The surgical vision system of claim 1, wherein the infrared source is configured to provide infrared light to tissue through an end of an endoscope, and the infrared camera is configured to receive infrared light from tissue through the end of the endoscope.

3. The surgical vision system of claim 1, wherein the infrared source is configured to provide infrared light to the tissue through an end of a laparoscope, and the infrared camera is configured to receive infrared light from the tissue through the end of the laparoscope.

4. The surgical vision system of claim 1, wherein the infrared camera is operable at least at a first wavelength in the infrared band of 0.8 to 4.6 microns.

5. The surgical vision system of claim 4, wherein the first wavelength is in the infrared band of 1.8 to 4.6 microns.

6. The surgical vision system of claim 4, wherein the infrared source is operable at least at a second wavelength in the infrared band of 0.8 to 4.6 microns.

7. The surgical vision system of claim 6, wherein the second wavelength is in the infrared band of 1.8 to 4.6 microns.

8. The surgical vision system of claim 4, wherein the first wavelength lies between 2.5 and 3 microns.

9. The surgical vision system of claim 1, where the image processing system is further adapted with image processing code to prepare a composite image derived from both the optical image and the image of rate of elevation or decay of temperature of the tissue.

10. The surgical vision system of claim 1, wherein the image of rate of elevation or decay of temperature of the tissue comprises multiple pixels each depicting rate of change of temperature.

11. A surgical vision system for imaging thermal energy of a tissue, comprising:
an infrared camera configured to provide images of tissue at infrared wavelengths and located in known orientation with respect to a camera operating in the visible spectrum;
an infrared source, located on a secondary instrument, configured to provide infrared light to tissue; and
an image processing system configured to determine the location and orientation of the secondary instrument by identifying where the infrared energy was deposited, to display images of heat capacity of the tissue derived from the images of tissue at infrared wavelengths, the images of heat capacity of the tissue derived by fitting an exponential function to from the images of tissue at infrared wavelengths and comprising images indicative of a cooling rate of the tissue.

12. The surgical vision system of claim 11, wherein the secondary instrument with the infrared source is fitted with multiple sources positioned in a specific pattern so that the image processing system can identify an orientation of the secondary instrument from the deposited infrared energy.

13. The surgical vision system of claim 12, wherein the secondary instrument is configured to sense at least one additional tissue property including at least one of electrical bioimpedance, optical scattering, optical absorption, and tissue density.

14. The surgical vision system of claim 13, wherein the at least one additional tissue property sensed is a property known to be a function of tissue temperature for at least one tissue type such that heating the tissue with the infrared source causes the additional tissue property to change.

15. A method of imaging tissue comprising:
positioning an instrument near the tissue, the instrument being selected from the group consisting of a laparoscope and an endoscope and comprising a mid-wavelength infrared source and a mid-wavelength infrared imager;
using the infrared source to apply high-power infrared light to the tissue, and thereby heating the tissue;
disabling the infrared source;
acquiring a sequence of infrared images of the tissue while allowing heated tissue to cool; and
processing the sequence of infrared images to produce an image depicting tissue cooling rate by fitting a function to pixels of the sequence of infrared images, the function being a first or second order exponential decay function.

16. The method of claim 15, further comprising:
obtaining an optical image of the tissue with an optical imaging device of the instrument; and
preparing a composite image derived from both the optical image and the image depicting tissue cooling rate.

17. A method of imaging tissue comprising:
positioning an instrument selected from the group consisting of a laparoscope and an endoscope near the tissue, the instrument comprising a mid-wavelength infrared imager;
positioning a second instrument near the tissue, the second instrument having a high-power infrared source;
using the infrared source to apply high-power infrared light to the tissue, and thereby heating the tissue;
disabling the infrared source;
acquiring at infrared images of the tissue;
processing the infrared images to produce an image depicting a heated area of the tissue, and an image depicting a rate of change of temperature in the heated area of the tissue by fitting an exponential function to pixels of the infrared images of the tissue.

* * * * *